United States Patent [19]
Lane et al.

[11] Patent Number: 5,837,466
[45] Date of Patent: Nov. 17, 1998

[54] DEVICES AND METHODS FOR DETECTING NUCLEIC ACID ANALYTES IN SAMPLES

[75] Inventors: David J. Lane, Wheaton; Michael P. Farrell, Sugar Grove, both of Ill.

[73] Assignee: Vysis, Inc., Downers Grove, Ill.

[21] Appl. No.: 768,177

[22] Filed: Dec. 16, 1996

[51] Int. Cl.⁶ .............................. C12Q 1/68; C12P 19/34; C07H 21/02; C07H 21/04
[52] U.S. Cl. .................... 435/6; 435/91.2; 435/91.21; 435/91.3; 435/91.31; 536/24.3
[58] Field of Search ............................ 435/6, 91.2, 91.21, 435/91.31, 91.3, 91.52; 436/94; 536/24.3; 935/76, 77

[56] References Cited

U.S. PATENT DOCUMENTS

| | | | |
|---|---|---|---|
| 4,786,600 | 11/1988 | Kramer et al. | 435/320.1 |
| 4,988,617 | 1/1991 | Landegren et al. | 435/6 |
| 5,112,734 | 5/1992 | Kramer et al. | 435/6 |
| 5,399,491 | 3/1995 | Kacian et al. | 435/91.21 |
| 5,407,798 | 4/1995 | Martinelli et al. | 435/6 |
| 5,610,287 | 3/1997 | Nikiforov et al. | 536/24.3 |
| 5,616,478 | 4/1997 | Chetverin et al. | 435/91.2 |

FOREIGN PATENT DOCUMENTS

| | | |
|---|---|---|
| WO 92/12261 | 7/1992 | WIPO . |
| WO 93/22461 | 11/1993 | WIPO . |
| WO 94/16105 | 7/1994 | WIPO . |
| WO 94/16106 | 7/1994 | WIPO . |
| WO 94/16108 | 7/1994 | WIPO . |

OTHER PUBLICATIONS

Burg et al., "Real–Time Flourescence Detection of RNA Amplified by Qβ Replicase", *Analytical Biochemistry*, 230:263–272, (1995).

Dolinnaya et al., "The use of BrCN for assembling modified DNA . . . with water–soluble carbodiimide", *Nucleic Acids Research*, 19:3067–3071, (1991).

Dolinnaya et al., "Site–directed modification of DNA duplexes by chemical ligation", *Nucleic Acids Research*, 16:3721–3738, (1988).

Dolinnaya et al., "Oligonucleotide circulation by template–directed chemical ligation", *Nucleic Acids Research*, 21:5403–5407, (1993).

Moody et al., "Evolution of Host Cell RNA into Efficient Template RNA by . . . in Untemplated Reactions", *Biochemistry*, 33:13836–13847, (1994).

Persing, "In Vitro Nucleic Acid Amplification Techniques", *Diagnostic Molecular Microbiology*, pp. 51–77, (1993).

Strobel et al., "Efficient Ligation of a Highly Structured RNA using T4 DNA Ligase", *Editorial Comments*, 19:89–91 (1992).

Tyagi et al., "Molecular Beacons: Probes that Fluoresce upon Hybridization", *Nature Biotechnology*, 14:303–308, (1996).

Primary Examiner—John L. LeGuyader
Assistant Examiner—Thomas G. Larson
Attorney, Agent, or Firm—Norval B. Galloway

[57] ABSTRACT

The invention provides devices and methods for use in detecting nucleic acid analytes in samples. The devices each include a solid support to which is bound a two-dimensional distribution or field of nucleic acid probes that each bind to a nucleic acid analyte, which is detected by use of amplification methods.

25 Claims, 11 Drawing Sheets

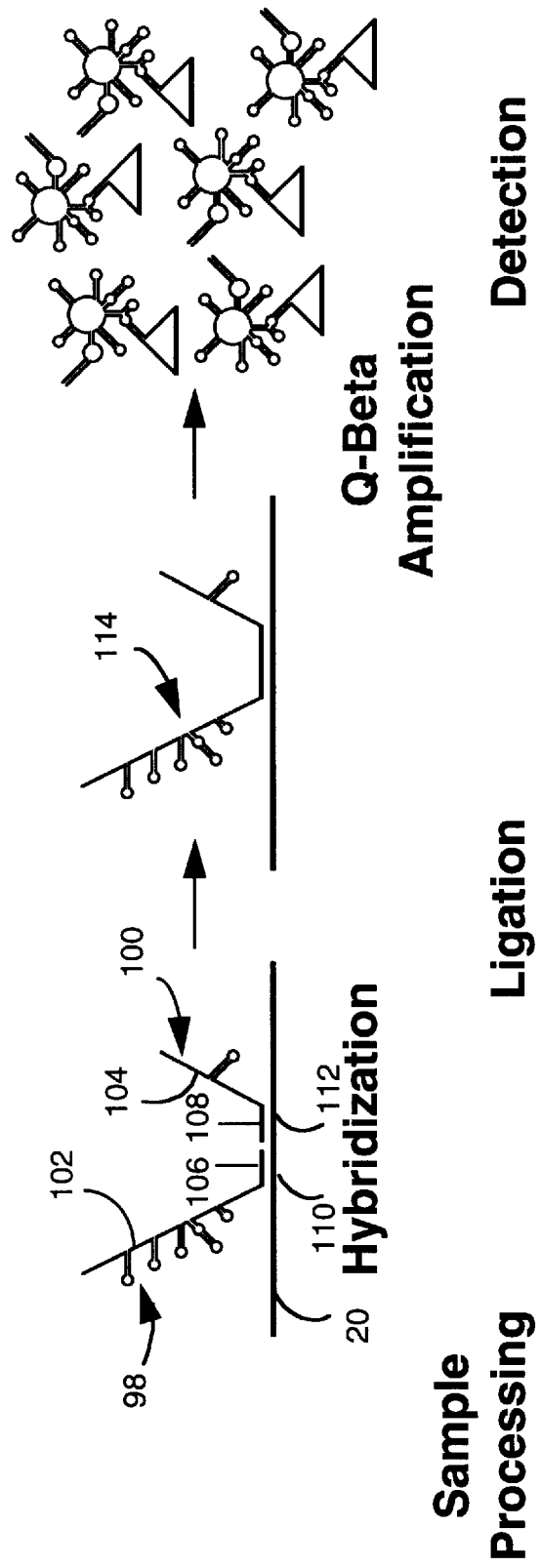

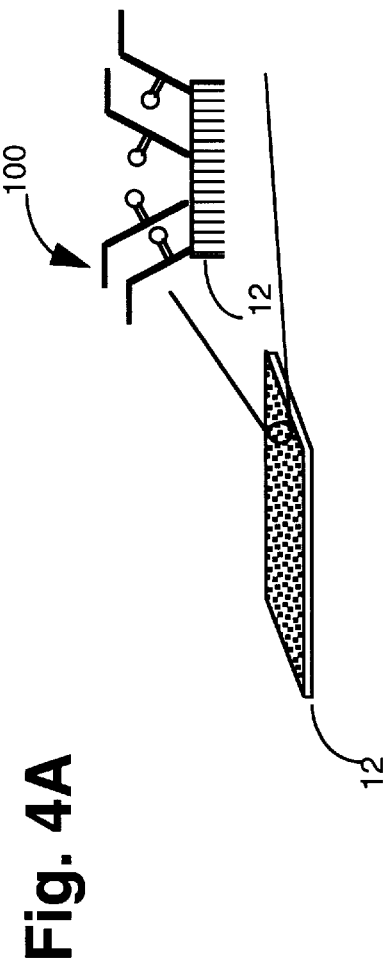
Fig. 4A
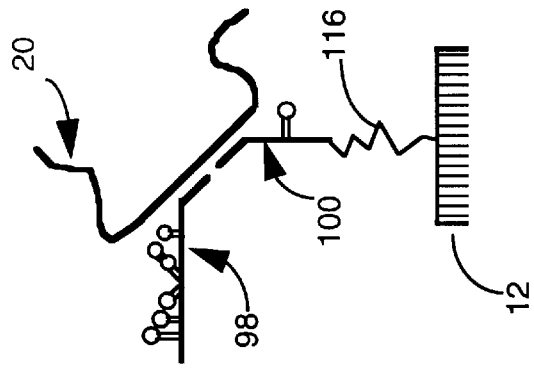
Fig. 4B
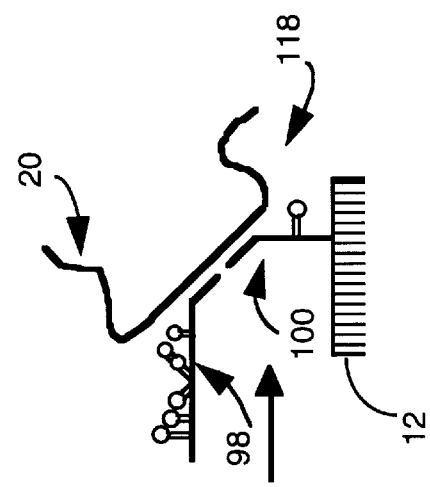
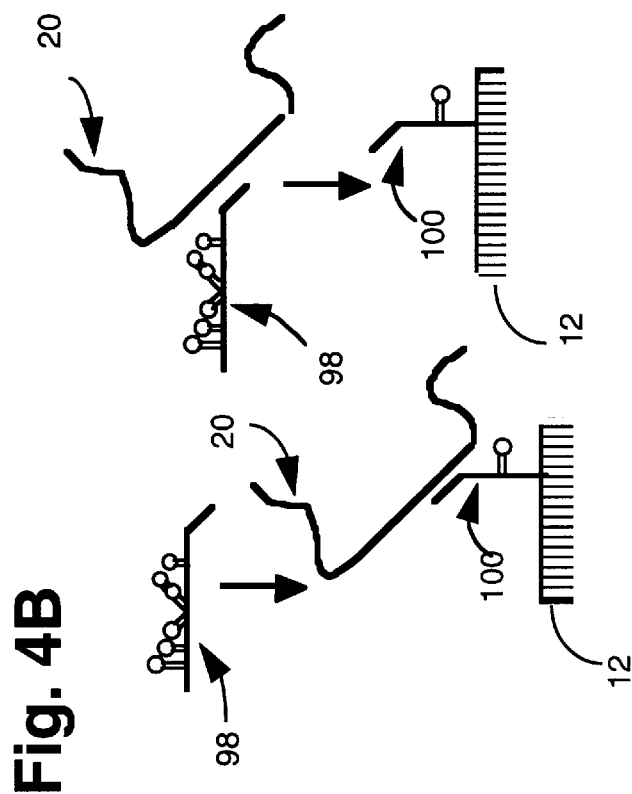
Fig. 4C

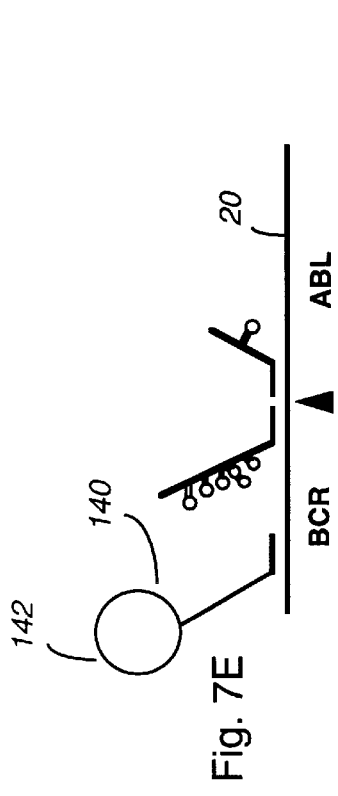
Fig. 7E
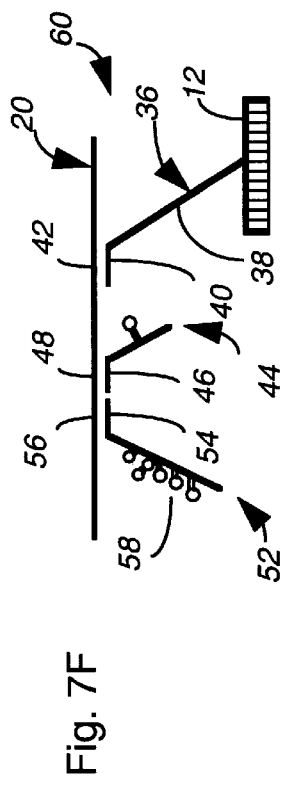
Fig. 7F
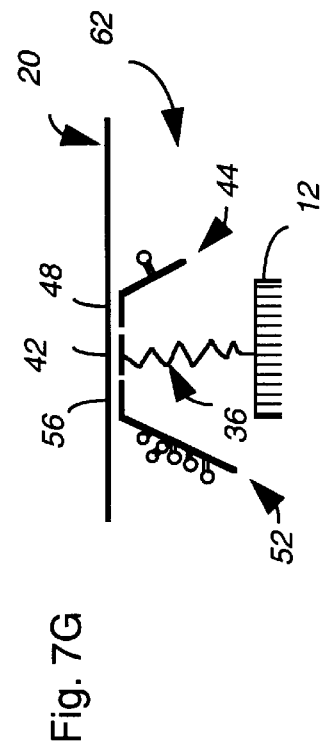
Fig. 7G
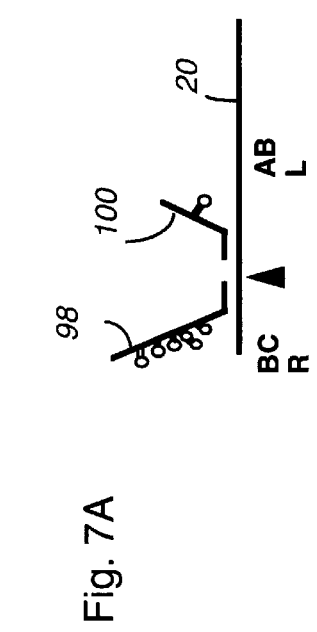
Fig. 7A
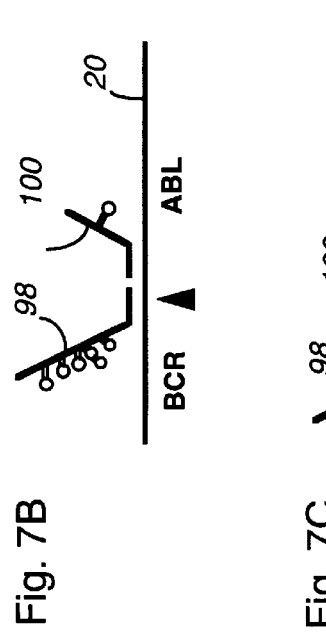
Fig. 7B
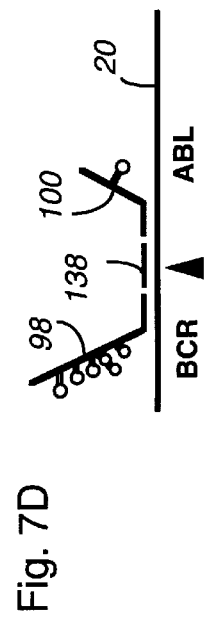
Fig. 7C
Fig. 7D

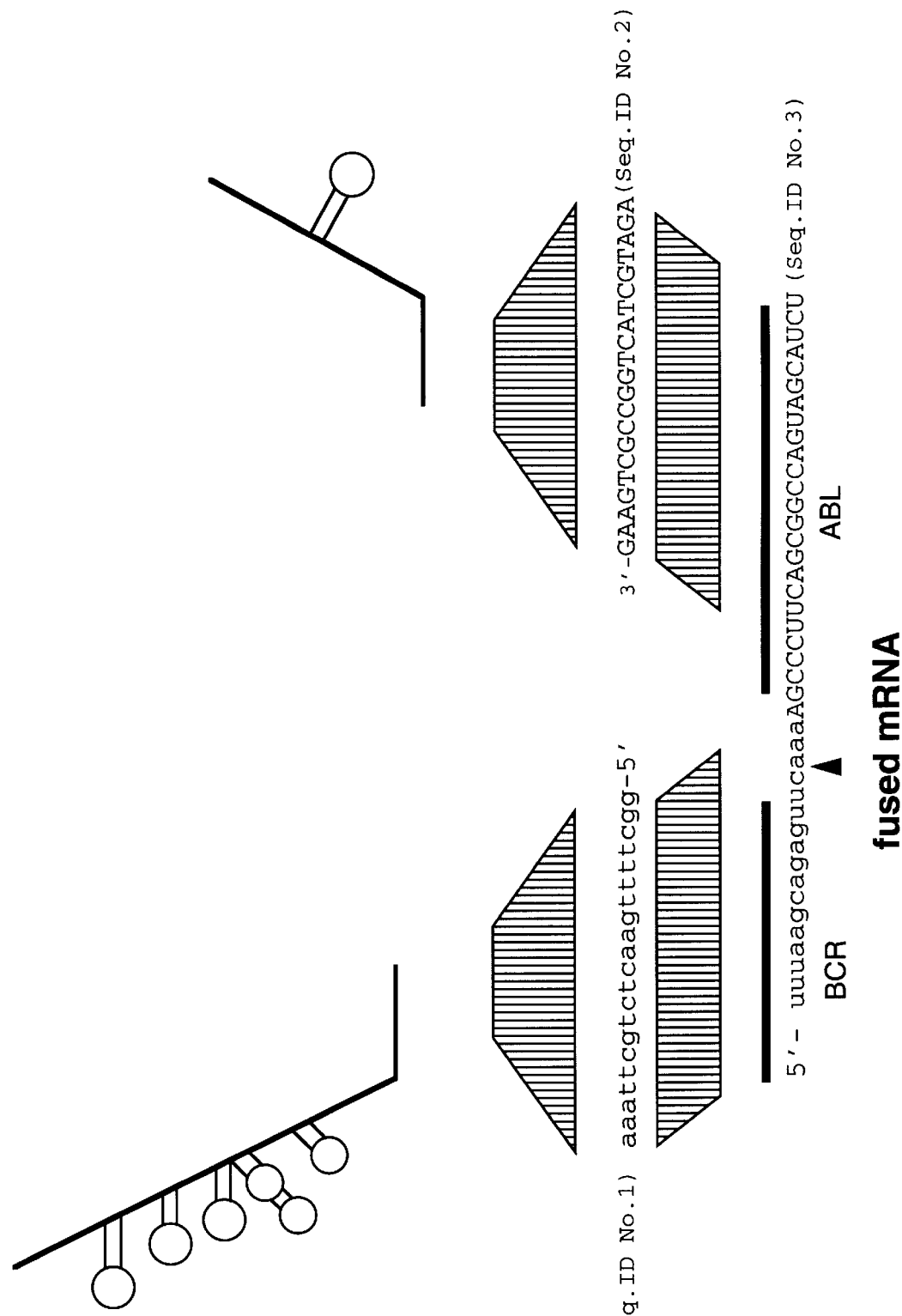

DEVICES AND METHODS FOR DETECTING NUCLEIC ACID ANALYTES IN SAMPLES

BACKGROUND OF THE INVENTION

The invention relates to devices and methods for detecting nucleic acid analytes in samples.

The detection of analytes present in trace amounts in samples for use in, e.g., medical diagnostics, requires sensitive and specific methods. Detection of such analytes can be hindered by the presence of substances present in higher concentrations in the samples. This problem is compounded if the analytes do not have physical or chemical properties that render them easy to detect.

SUMMARY OF THE INVENTION

The invention provides assay devices that include two-dimensional distributions or fields of probes bound to a surface of a solid support. The devices of the invention can be used in methods for detecting analyte nucleic acids in samples. In these methods, samples are applied to the surface of the solid support containing the field of probes, and analytes in the sample that bind to the probes are detected by an amplification method.

Accordingly, in one aspect the invention features an assay device for detecting the presence of a nucleic acid analyte in a sample. The device of the invention includes a solid support (e.g., a glass plate), to which is bound a two-dimensional field of analyte-specific nucleic acid probes, each of which includes (1) a first end bound to the support and including a portion of an autocatalytically replicable nucleic acid (e.g., a nucleic acid, such as a midivariant nucleic acid, that is replicable by Q-beta replicase), and (2) a second end including an analyte-binding segment.

The invention also includes a method for detecting the presence of a nucleic acid analyte in a sample. In this method, the sample is first applied to a solid support, to which is bound a two-dimensional field of first analyte-specific nucleic acid probes, each of which has (i) a first end bound to the support and including a portion of an autocatalytically replicable nucleic acid (e.g., a nucleic acid, such as a midivariant nucleic acid, that is replicable by Q-beta replicase), and (ii) a second end including a first analyte-binding segment. The first analyte-binding segment of each of the first probes used in this method hybridizes to a first region of the analyte. A second nucleic acid probe that (i) has a second analyte-binding segment that hybridizes to a second region of the analyte, and (ii) includes a remainder of the autocatalytically replicable nucleic acid, is then applied to the solid support. The first and second regions of the analyte are adjacent nucleotide segments, and the analyte, the first probe, and the second probe hybridize together on the support to form a complex that includes a complete autocatalytically replicable nucleic acid.

A diffusion limiting matrix (made of, e.g., gelatin, agarose, polyacrylamide, or a combination thereof) is then applied to the solid support, and the complete autocatalytically replicable nucleic acid is amplified to generate an amplified product, which is detected as a measure of the presence of the analyte in the sample. Optionally, this method can also include a step of ligating the first and second probes in the complex together to form the complete autocatalytically replicable nucleic acid. In addition, the method can include a washing step, in which any unbound first or second probes are removed from the complex. Also, the sample can be applied to the support in this method prior to being contacted with the second probe, or the sample can be contacted with the second probe prior to being applied to the support.

The amplification step in this method can be carried out in the presence of a fluorescent intercalating dye, so that the detection step can be carried out by monitoring the device for the presence of the dye. The detection step can also be carried out by employing a fluor-quencher pair. This detection method can be used in variations of this method, in which multiple analytes are simultaneously detected in the sample by the use of multiple fluor-quencher pairs that include distinguishable fluorescent moieties.

This method can also include a step in which the concentration of the analyte in the sample is determined. For example, as is described further below, the concentration of the analyte in the sample can be determined by counting colonies of amplified product formed on the solid support.

The invention also includes an assay system for detecting a nucleic acid analyte in a sample. This assay system includes a solid support to which is bound a two-dimensional field of first analyte-specific nucleic acid probes, each of which includes (i) a first end bound to the support and including a portion of an autocatalytically replicable nucleic acid, and (ii) a second end including a first analyte-binding segment. The first analyte-binding segment of each of the first probes in this system hybridizes to a first region of the analyte. The system further includes a second nucleic acid probe, which includes (i) a second analyte-binding segment that hybridizes to a second region of the analyte, and (ii) a remainder of the autocatalytically replicable nucleic acid. The first and second regions of the analyte detected using this system include adjacent nucleotide segments, and binding of the first and second probes to the analyte permits amplification of the autocatalytically replicable nucleic acid.

Another assay system for detecting a nucleic acid analyte in a sample that is included in the invention includes a solid support to which is bound a two-dimensional field of capture probes that each include a capture segment that hybridizes to a capture region of the analyte. Also included in this assay system is (i) a first nucleic acid probe having a first segment that hybridizes to a first region of the analyte, and (ii) a second nucleic acid probe having a second segment that hybridizes to a second region of the analyte. In this system, binding of the capture probes and the first and second probes to the analyte permits amplification of a detectable product.

This assay system can be used in a method for detecting the presence of a nucleic acid analyte in a sample. In this method, the sample is contacted with the bound capture probes and the first and second probes described above, the capture and first regions of the analyte are adjacent nucleotide segments, the capture and second regions of the analyte are adjacent nucleotide segments, the first nucleic acid probe further includes a portion of an autocatalytically replicable nucleic acid molecule, the second nucleic acid probe further includes a remaining portion of the autocatalytically replicable nucleic acid molecule, and the contacting permits the analyte, the first probe, and the second probe to hybridize together on the support to form a complex including a complete autocatalytically replicable nucleic acid. A diffusion limiting matrix is then applied to the solid support, and the complete autocatalytically replicable nucleic acid is amplified to generate an amplified product, which can be detected as a measure of the presence of the analyte in the sample.

In a variation of the assay system described above, the first and second regions of the analyte can be adjacent nucleotide segments, the first nucleic acid probe can further include a portion of an autocatalytically replicable nucleic acid molecule, and the second nucleic acid probe can further include a remaining portion of the autocatalytically replicable nucleic acid molecule.

This variation can also be used in a method for detecting the presence of a nucleic acid analyte in a sample. In this method, the sample is contacted with the bound capture probes and the first and second probes described above, the capture and first regions of the analyte are adjacent nucleotide segments, the first nucleic acid probe further includes a portion of an autocatalytically replicable nucleic acid molecule, the second nucleic acid probe further includes a remaining portion of the autocatalytically replicable nucleic acid molecule, and the contacting permits the analyte, the first probe, and the second probe to hybridize together on the support to form a complex including a complete autocatalytically replicable nucleic acid. A diffusion limiting matrix is then applied to the solid support, amplification of the complete autocatalytically replicable nucleic acid is carried out to generate an amplified product, and the amplified product is detected as a measure of the presence of the analyte in the sample.

In an alternative assay system, the capture and first regions of the analyte are adjacent nucleotide segments, the capture and second regions of the analyte are adjacent nucleotide segments, the first nucleic acid probe further contains a portion of an autocatalytically replicable nucleic acid molecule, and the second nucleic acid probe further includes a remaining portion of the autocatalytically replicable nucleic acid molecule.

The invention includes an additional method for detecting the presence of a nucleic acid analyte in a sample. In this method, the sample is contacted with a solid support to which is bound a two-dimensional field of first analyte-specific nucleic acid probes, each of which has (i) a first end bound to the support, and (ii) a second end including a first analyte-binding segment. A diffusion limiting matrix is applied to the support, and amplification is carried out using the polymerase chain reaction, ligase chain reaction, transcription-mediated amplification, nucleic acid sequence-based amplification, or strand displacement amplification, in a manner dependent upon the presence of both the first probe and the specified analyte nucleic acid, and in such a manner that the products of such amplification reaction are restrained to form localized foci on the two-dimensional layer. The amplified product is then detected as a measure of the presence of the analyte in the sample.

Amplification methods that can be used in the invention include known methods, for example, (i) target amplification, e.g., the polymerase chain reaction ("PCR"; Saiki et al., Science 230:1350–1354, 1985), a transcription-based amplification system ("TAS"; Kwoh et al., Proc. Natl. Acad. Sci. USA 86:1173–1177, 1989), the self-sustained sequence reaction ("3SR"; Guatelli et al., Proc. Natl. Acad. Sci. USA 87:1874–1878, 1990), transcription-mediated amplification ("TMA"; U.S. Pat. No. 5,399,491; WO 93/22461), nucleic acid sequence-based amplification ("NASBA"; Compton, Nature (London) 350:91–92, 1991), strand displacement amplification ("SDA"; Walker et al., Nucleic Acids Research 20:1691–1696, 1992); and (ii) probe amplification, e.g., Q-beta replicase ("QBR"; Lizardi et al., Bio/Technology 6:1197–1202, 1988), ligase amplification reaction ("LAR"; Wu et al., Genomics 4:560–569, 1989), and ligase chain reaction ("LCR"; Barany, Proc. Natl. Acad. Sci. USA 88:189–193, 1991). These and other amplification methods that can be used in the invention are reviewed by Pershing et al. ((eds.) Diagnostic Molecular Microbiology, Principles and Applications, American Society for Microbiology, Washington, 1993). In principle, any amplification system can be used in the invention.

A pair of nucleic acid molecules (or two regions within a single nucleic acid molecule) are said to "hybridize" to each other if they form a duplex by base pairing interactions between them. As is known in the art, hybridization between nucleic acid pairs does not require complete complementarity between the hybridizing regions, but only that there is a sufficient level of base pairing to maintain the duplex under the hybridization conditions used.

The members of a pair of molecules (e.g., a pair of nucleic acids) are said to "specifically bind" to each other if they bind to each other with greater affinity than to other, non-specific molecules. For example, a nucleic acid probe can be described as specifically binding to an analyte nucleic acid if it hybridizes to form a specific duplex with the analyte by base pairing interactions.

Alternative methods of specifically binding nucleic acid molecules are known in the art and can be used in the invention. For example, nucleic acid analogs (i.e., non-natural variations of nucleic acids, see, e.g., Cohen, (ed.), *Oligodeoxynucleotides: Antisense Inhibitors of Gene Expression,* CRC Press Inc., Fla., USA, 1989; Uhlmann et al., Chem. Rev., 90:543–584, 1990) and non-nucleic acid-based polymers, such as peptide nucleic acids ("PNA"; Nielsen et al., Science 254:1479–1500, 1991; Egholm et al., J. Am. Chem. Soc. 114:1895–1897, 1992; Egholm et al., J. Am. Chem. Soc. 114:9677–9678, 1992) can be used. An additional binding method that can be used to specifically bind nucleic acids to the two-dimensional field of the invention is triple helix formation (Felsenfeld et al., Biochim. Biophys. Acta. 26:457–468, 1957; Thuong et al., Angewandte Chemie 32:666–690, 1993; Chubb et al., *Trends Biotech.* 10:132–136, 1992; Moffat, Science 252:1374–1375, 1991).

Autocatalytically replicable nucleic acids that can be used in the invention comprise nucleic acids that are replicable by QBR, for example, midivariant RNAs, e.g., midivariant-1 (MDV-1), and variants of MDV-1, including, without limitation, minivariant RNA, microvariant RNA, nanovariant RNA, and variants thereof. These molecules are typically modified to include sequences of analyte-specific nucleic acids. In embodiments of the invention in which amplification methods other than QBR are employed, the signal-generating nucleic acids simply need to be replicable by amplification systems that are well known in the art (e.g., see above).

A probe can be bound to a solid support directly, e.g., via covalent bonds, or indirectly via a spacer, e.g., a polyadenosine or other nucleic acid sequence, a protein ligand, such as streptavidin, or an organic polymer (see below).

Solid supports that can be used in the invention include glass, paper, gels, films, membranes, e.g., a nitrocellulose membrane, or plastics. In general, any solid planar surface can be used, as long as nucleic acids can be bound to the surface.

The invention provides several advantages. For example, the diffusion path of an analyte that is required for it to be detected using the devices of the invention is "straight down." That is, the analyte can contact the solid support and form a "productive" complex (see, e.g., FIG. 1A) at any place on the surface of the solid support; lateral diffusion is not required. In contrast, other array-type assays known in the art employ discrete loci (e.g., spots, squares, etc.) for detecting different analytes on a single device. For example, in Affymetrix-type arrays, up to 16,000 spots, each containing a different probe sequence, are affixed to a surface of a solid support in a specific pattern. The analyte nucleic acid-containing sample is applied to the surface of such an array, and during hybridization, the analyte molecule must diffuse down to the surface of the array, as in the present invention, but also it must diffuse laterally, to find its cognate spot of probe molecule. This requirement of lateral diffusion limits both the sensitivity and the kinetics of the hybridization reaction.

Unless otherwise defined, all technical and scientific terms used herein have the same meaning as commonly understood by those of ordinary skill in the art to which this invention belongs. Although methods and materials similar or equivalent to those described herein can be used in the practice or testing of the invention, some preferred methods and materials are described below. All publications, patent applications, patents, and other references mentioned herein are incorporated by reference in their entirety. In case of a conflict, the present specification will control. In addition, the described materials and methods are illustrative only and are not intended to be limiting.

Other features and advantages of the invention will be apparent from the following detailed description and the claims.

BRIEF DESCRIPTION OF THE DRAWINGS

FIG. 3 is a schematic representation of a QBR ligation-based binary probe assay.

FIGS. 4A–4F are schematic representations of methods employing devices of the invention, in which the probe bound to the solid surface includes a portion of an autocatalytically replicable nucleic acid.

FIGS. 7A–7G are schematic representations of variations in binary probe design that are within the scope of invention.

FIG. 8 is a schematic representation of 3' and 5'-half probes that can be used in detecting the major BCR/ABL junction found in CML patients.

DETAILED DESCRIPTION

The invention provides devices and methods for sensitive and quantitative detection of nucleic acid analytes in samples. A central feature of the devices of the invention is that they each include a solid support to which is bound a two-dimensional, random distribution or field of nucleic acid probes that each bind to a nucleic acid analyte. Once a nucleic acid analyte is bound to a probe of the device, analyte-specific amplification is carried out to generate an amplification product, which is detected in the field as a measure of the presence of the nucleic acid analyte in the sample. Amplification produces individual colonies of the amplification product, which are centered around each of the original nucleic acid probes, thus forming detectable circular colonies or "spots" on the solid support.

Figure 1A:
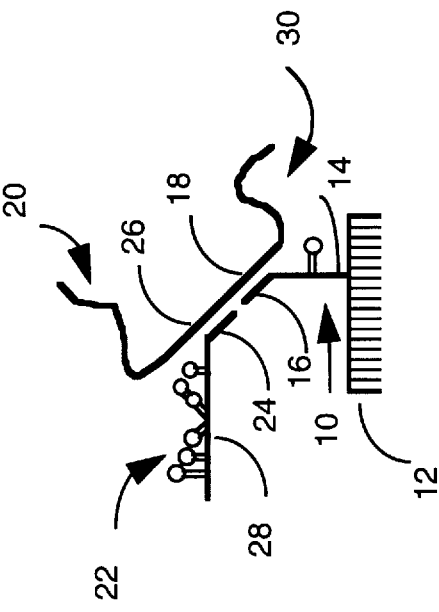
FIGS. 1A and 1B are schematic representations of assay formats included in the invention.

The devices and methods of the invention can embody a number of different formats. For example, as illustrated in FIG. 1A, the probe 10 bound to the solid support 12 of the device can include a first end 14 that is bound to the solid support 12 and includes a portion of an autocatalytically replicable nucleic acid 15, and a second end 16 that includes a first analyte-binding segment, which hybridizes to a first region 18 of a nucleic acid analyte 20. This device can be used in methods in which it is contacted with (1) a sample containing a nucleic acid analyte 20, and (2) a second nucleic acid probe 22 that contains a second analyte-binding segment 24, which hybridizes to a second region 26 of the nucleic acid analyte 20, and a remainder 28 of the autocatalytically replicable nucleic acid.

In this format, the first 18 and second 26 regions of the analyte 20 can be adjacent nucleotide segments, so that when the analyte 20, first probe 10, and second probe 22 hybridize together on the support 12 to form a complex 30, a complete template for autocatalytic replication, consisting of the first 10 and second 22 probes, is formed.

Figure 1B:
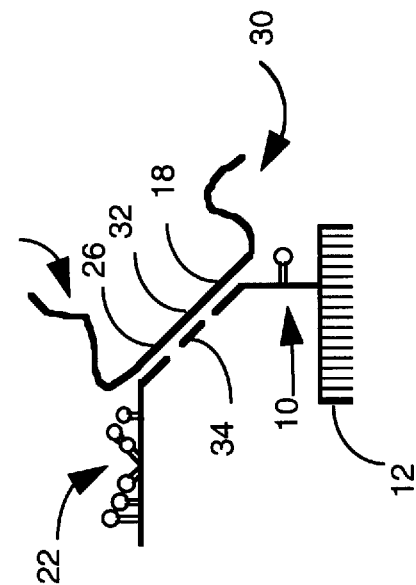

Alternatively, as illustrated in FIG. 1B, the first 18 and second 26 regions of the analyte 20 can be separated by a third analyte region 32, to which a third probe 34 binds. In this case, the first 18 and second 26 regions of the analyte flank, and are adjacent to, the third region 32, so that when the analyte 20, first probe 10, second probe 22, and third probe 34 hybridize together on the support 12 to form a complex 30, a complete template for autocatalytic replication, consisting of the first 10, second 22, and third 34 probes, is formed.

In the two examples described above, the probes forming the template for autocatalytic replication can, if desired, be ligated together using conventional methods, such as, e.g., enzymatic methods (for example, by employing T4 DNA ligase (European Patent Applications EP 94/906626.0 and EP 94/906682.3), an RNA ligase, or a ribozyme ligase), chemical methods (see, e.g., Herrlein et al., Nucleic Acids Research 22:5076–5078; Dolinnaya et al., Nucleic Acids Research 16:3721, 1988; Dolinnaya et al., *Nucleic Acids Research* 19:3067–3072, 1991; Dolinnaya et al., Nucleic Acids Research 21:5403–5407, 1993) and photochemical methods (see, e.g., U.S. Pat. No. 5,219,734). In addition, the order in which the samples and probes are contacted with the solid support can be varied.

In another example of a device included in the invention, as illustrated in FIG. 7F, the first probe 36, which is bound to the solid support 12 of the device, includes a first end 38 that is bound to the solid support 12 and a second end 40 that includes a first analyte-binding segment, which hybridizes to a first region 42 of a nucleic acid analyte 20. This device can be used in methods in which the solid support 12 is contacted with (1) a sample containing an analyte 20, (2) a second nucleic acid probe 44 that contains a second analyte-binding segment 46 that hybridizes to a second region 48 of the analyte 20, and a portion 50 of an autocatalytically replicable nucleic acid, and (3) a third nucleic acid probe 52 that contains a third analyte-binding segment 54, which hybridizes to a third region 56 of the analyte 20, and a remainder 58 of the autocatalytically replicable nucleic acid.

In this format, the second 48 and third 56 regions of the analyte 20 can be adjacent nucleotide segments, so that when the analyte 20, second probe 44, and third probe 52 hybridize together on the support 12 to form a complex 60, a complete template for autocatalytic replication is formed between the second 44 and third 52 probes. In this case, the first probe 36 bound to the solid support 12 serves only as a capture probe, binding the complex 60 formed between the nucleic acid analyte 20 and the second 44 and third 52 probes to the solid support 12. Also, the second 44 and third 52 probes can, if desired, be ligated together when bound to the analyte 20. Further, the order of addition of the probes and sample to the solid support 12 can be varied.

Alternatively, as illustrated in FIG. 7G, the second 48 and third 56 regions of the analyte 20 can each flank, and be adjacent nucleotide segments with, the first region 42 of the analyte 20. When the analyte 20, first probe 36 (e.g., including a nucleic acid and a linker), second probe 44, and third probe 52 hybridize together on the support 12 to form a complex 62, a complete template for autocatalytic replication, consisting of the first 36, second 44, and third 52 probes, is formed.

Figure 9A:
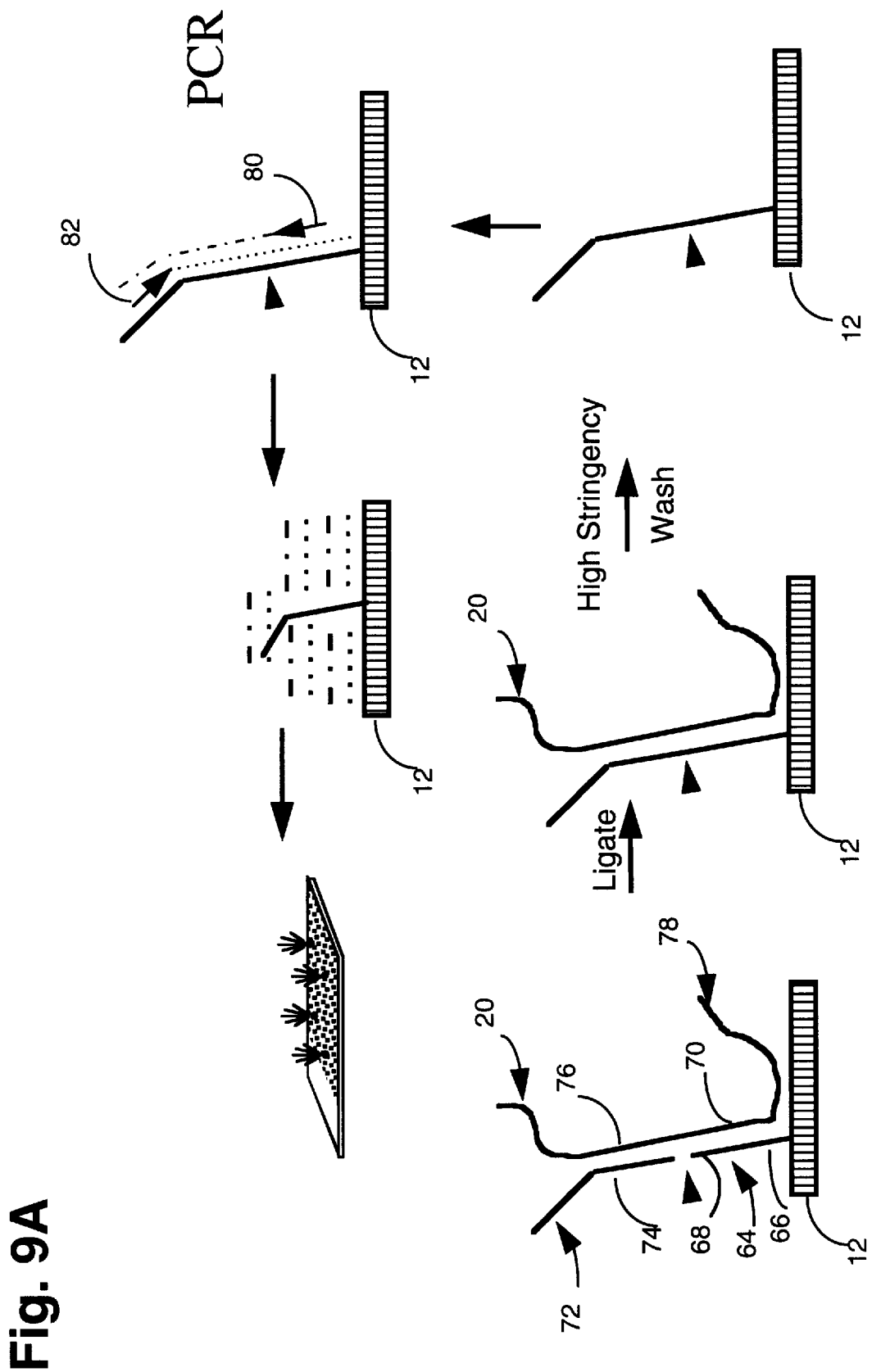
FIGS. 9A and 9B are schematic representations of methods of the invention that employ PCR amplification.

In another example of a device included in the invention, as illustrated in FIG. 9A, the first probe 64, which is bound to the solid support 12 of the device, includes a first end 66 that is bound to the solid support 12 and a second end 68 that includes a first analyte-binding segment, which hybridizes to a first region 70 of a nucleic acid analyte 20. This device can be used in methods in which the solid support 12 is contacted with (1) a sample containing an analyte 20, and (2) a second nucleic acid probe 72 that contains a second analyte-binding segment 74, which hybridizes to a second region 76 of the analyte 20.

In this format, the first 70 and second 76 regions of the analyte 20 are adjacent nucleotide segments, so that when the first probe 64, the analyte 20, and the second probe 72 hybridize together on the support 12 to form a complex 78, the first 64 and second 72 probes, are brought together by binding to the analyte nucleic acid 20, so that they can be ligated together. A high stringency wash is then carried out to remove unligated second probe 72 and analyte nucleic acid 20. The ligated product is then amplified by standard PCR. For example, if the first probe 64 is bound to the solid support by its 5' end, then a first primer 82 is used to copy the ligated product to make a first product, which is complementary to the ligated product. A second primer 80 then anneals to the first product and copies it, making a second product strand that is identical to the ligated product in the region between and including the two primers. PCR then operates on these first and second products to make a large number of first and second product strands, which are localized to the vicinity of the original ligated probe product by the diffusion limiting matrix. This spot can be detected by any of the means discussed above for the detection of QBR products, e.g., by detection of incorporated radioactivity, fluorescence, etc.

Figure 9B:
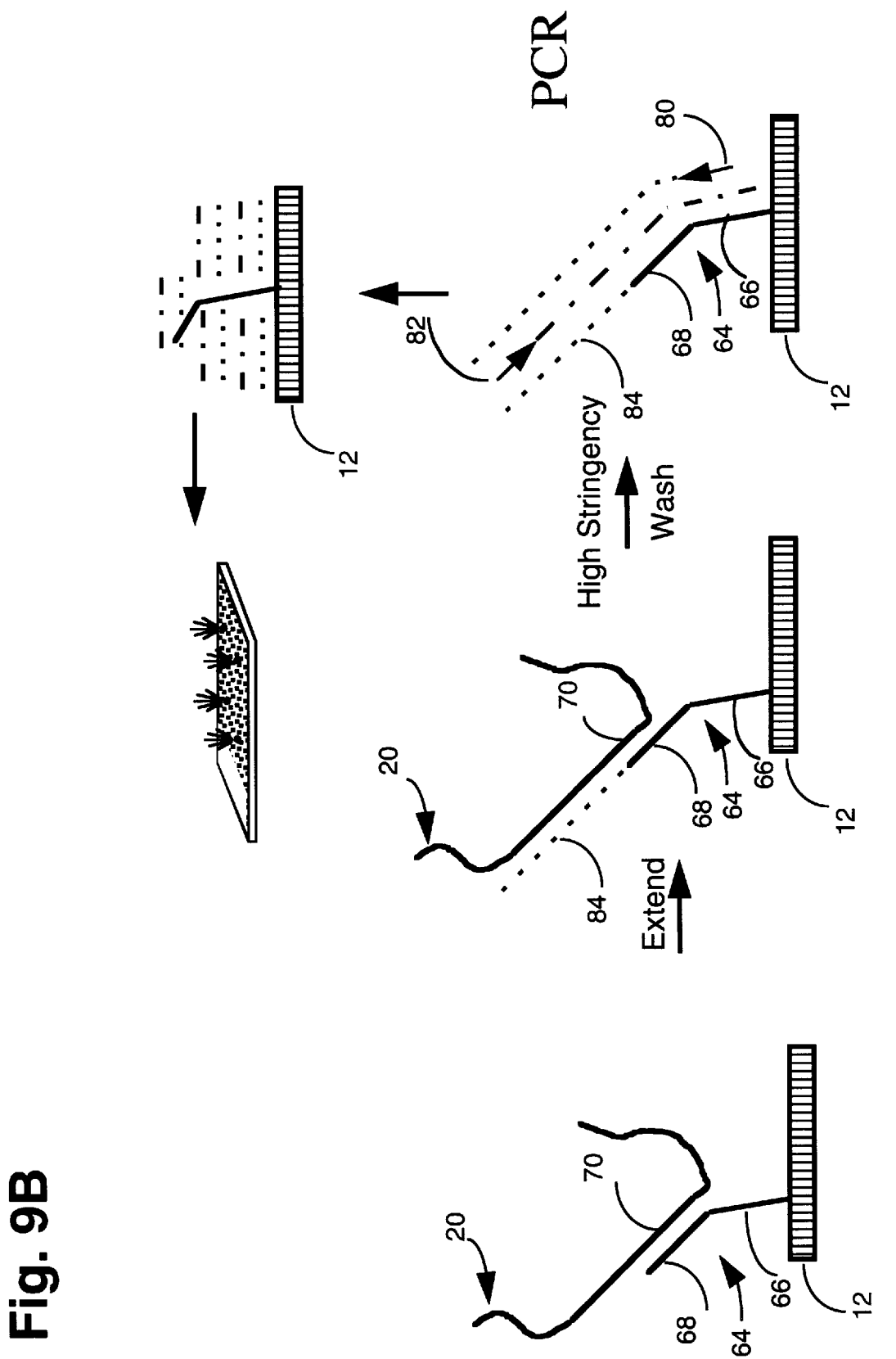

In a variation of this method, in which a ligation step is not required, the solid support 12 is contacted with the sample, but not the second probe (FIG. 9B). Complexes formed by specific hybridization between the first probe 64, which is bound to the solid support 12 via its 5' end, and the analyte nucleic acid 20 are washed, and the 3' end of the first probe 64 bound to the support 12 is extended, using the analyte nucleic acid 20 as a template. After a high stringency wash, the extended product is amplified by any of the standard target or probe amplification techniques listed in the introduction (e.g., PCR) to produce a detectable signal corresponding to the presence and location of the ligated product on the field of the device. For example, if PCR is used and the first probe 64 is attached to the support 12 by its 5' end, a first primer 80, identical to a portion of the first probe 64, and a second primer 82, complementary to a portion of the extended region 84 of the first probe 64, can be used to generate a detectable, amplified product.

The invention is described in further detail below with reference to the first example described above.

Figure 2A:
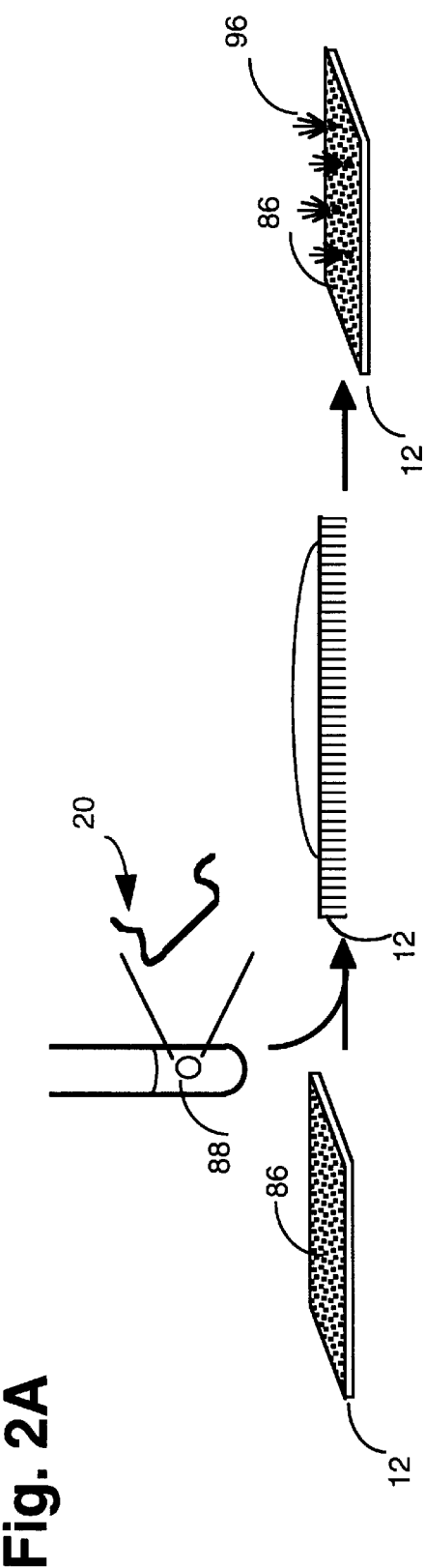
FIGS. 2A and 2B are schematic representations of a device of the invention and its use in methods for detecting nucleic acid analytes.
Figure 2B:
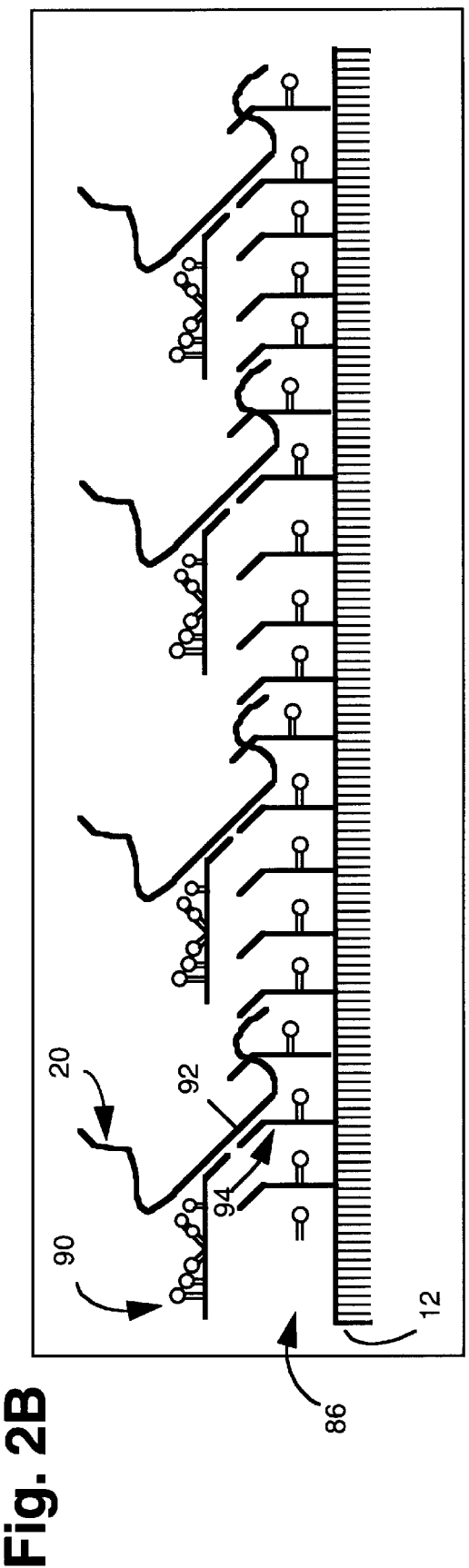

As discussed above, and illustrated in FIGS. 2A and 2B, the device of the invention is a field of analytespecific probes 86 coated on the surface of a solid support 12, such as a microscope slide. Preferably, the probes 86 are uniformly coated on the solid support 12, but they can be limited to specific locations, if desired. Analyte nucleic acid molecules 20 contained within, e.g., a clinical specimen 88, are applied to the solid support 12, where they diffuse to the surface of the solid support 12 and are captured by (i.e., hybridize to) the specific probes on the field 86. The analytes 20 are then simply detected or quantitated using an appropriate replication system, e.g., the QBR amplification system.

In this detection step, a second, analyte-specific probe 90 is hybridized to each analyte molecule 20 immediately adjacent to the hybridization site 92 of each one 94 of the probes 86 that is bound to the solid support 12. These two probes 90 and 94 can then be joined together to form a nucleic acid molecule that can be replicated or amplified by an enzyme, such as QBR. QBR amplification can then be used to form a spot of highly concentrated RNA product 96 in the immediate vicinity of the immobilized analyte molecule 20, which can easily be detected, e.g., with a fluorescence microscope. The number of such "spots" 96 on the solid support 12 corresponds to the number of analyte molecules 20 that originally bound the solid support 12.

As is discussed above, this and other embodiments of the invention employ autocatalytically replicable nucleic acid molecules, such as midivariant and related RNAs that are modified to include a sequence of analyte-specific nucleic acid, that can be amplified by enzymes, such as QBR. The use of such nucleic acid molecules and QBR in the invention is illustrated in FIG. 3, and is described further as follows.

Autocatalytically replicable nucleic acids are employed in binary probe assays in the invention. Accordingly, for use in the invention, they are split into two "half molecules" 98 and 100, neither of which can alone be replicated appreciably by QBR. Each half molecule contains two functional elements: a partial MDV sequence 102 (and 104) and a probe sequence 106 (and 108), which is complementary to, and thus capable of specific hybridization with, a target sequence 110 (and 112) in a nucleic acid analyte 20. The probe sequences 106 and 108 of the two half molecules 98 and 100 are chosen so that they hybridize to adjacent nucleotide segments 110 and 112 in the analyte 20. The two half molecules are individually referred to below as a 3'-half probe 98 and a 5'-half probe 100, based on the polarity of the nucleic acids of which they are made.

The designation "half molecule" or "half probe" is not intended to mean that such probes have to contain exactly "half" of a complete, autocatalytically replicable molecule. For example, the point of probe insertions can be about ⅓ of the way from the 5' end and about ⅔ from the 3' end. Other insertion points are known in the art (see, e.g., Burg et al., Anal. Biochem. 230:263–272, 1995). Replicable modifications of nucleic acids containing these modifications are also within the scope of the invention. Also, both half probes can consist of DNA or RNA. Alternatively, one half probe can consist of DNA and the other of RNA. Each half probe can also contain a combination of deoxyribonucleotides and ribonucleotides, or modifications thereof.

If the analyte nucleic acid 20 is present in the sample being assayed, both half molecules 98 and 100 hybridize in the configuration shown in FIG. 3. Half molecules bound in this manner can, optionally, be covalently joined together by a ligation step, which creates a complete detection probe 114 that is replicable by QBR, and thus is capable of generating an assay signal. However, amplification can be carried out even if the two half probes are not ligated together. Unligated half probes that are held in close proximity to one another and in approximately correct topology by the target nucleic acid (as shown in FIG. 4C) can be amplified by QBR. However, ligated half probes can be amplified with significantly greater sensitivity (10 to $10^6$-fold, depending upon the hybridization and washing conditions used).

Another significant advantage of employing a ligation step is that, following ligation, the ligated probe molecules are covalently linked to the solid support so that extremely high stringency wash conditions (such as would disrupt signal-generating complexes, e.g., as shown in FIG. 4C, where the 3'-half probes are not covalently attached to the solid support) can be used. Nevertheless, for applications requiring lower sensitivity, the elimination of one assay step, e.g., the ligation step, can be useful.

As is mentioned above, ligation of the half molecules can be effected using any of a variety of well known methods including, e.g., enzymatic methods (for example, by employing T4 DNA ligase, an RNA ligase, or a ribozyme ligase), chemical methods, and photochemical methods.

Figure 4E:
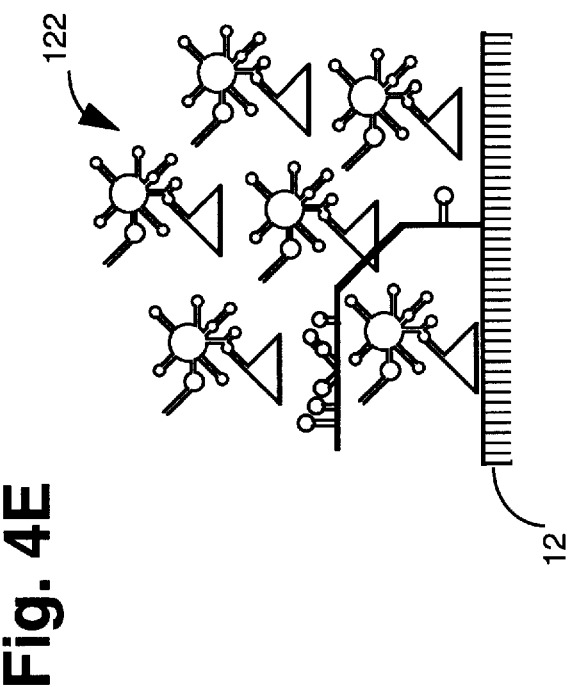

As is discussed above, and illustrated further in FIGS. 4A–4F, a central feature of the invention is that a probe, which can contain a half molecule 100 of a QBR detector probe, is uniformly dispersed and specifically attached to the surface of a solid support 12, such as a microscope slide or a similar surface, or to a portion thereof. Preferably, the 5'-half probe 100 is attached to the support 12 through its 5' end (FIG. 4A). The linkage can, optionally, include additional nucleotide or non-nucleotide spacers or "linker groups" 116 to promote efficient hybridization and replication. Alternatively, the 3'-half probe 98 can be attached to the support 12 through its 3' end. The probes illustrated in FIGS. 4A–4F are based on a particular QBR amplifiable construct called midivariant RNA. As mentioned above, a variety of other autocatalytically replicable nucleic acids can be used in the invention.

Following lysis of the sample, if required, during which the analyte nucleic acid 20 is rendered accessible for hybridization, the 3'-half probe 98, is added to the sample under conditions that promote specific hybridization with the analyte nucleic acid 20. Subsequently, or simultaneously, the sample is applied to the support and is allowed to form probe/analyte nucleic acid hybrids by nucleic acid hybridization. A variety of well known agents that promote or modify hybridization can be used in the invention. For example, the chaotropic agent guanidinium thiocyanate is a well known hybridization agent, which promotes both sample lysis and hybridization.

Depending upon the hybridization conditions used (e.g., salt type and concentration, temperature, probe concentration, the presence of accelerators, denaturants, and detergents; the length of "pre-hybridization" with the 3'-half probe 98, etc.; see above), a greater or lesser proportion of the analyte nucleic acids 20 may already have 3'-half probe 98 hybridized to it at the beginning of the hybridization on the solid support (FIG. 4B). Following an appropriate period of hybridization, a complex 118 containing a 5'-half probe 100, a nucleic acid analyte 20, and a 3'-half probe 98 is formed (FIG. 4C).

Figure 4F:
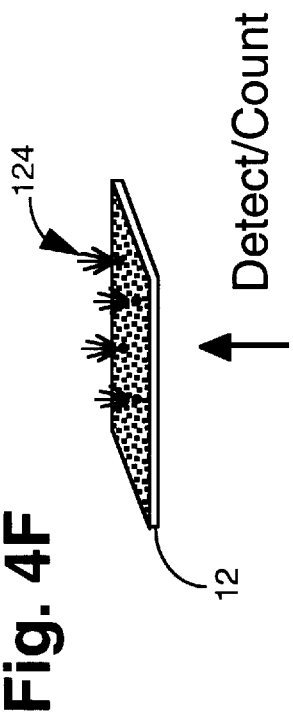
Figure 4D:
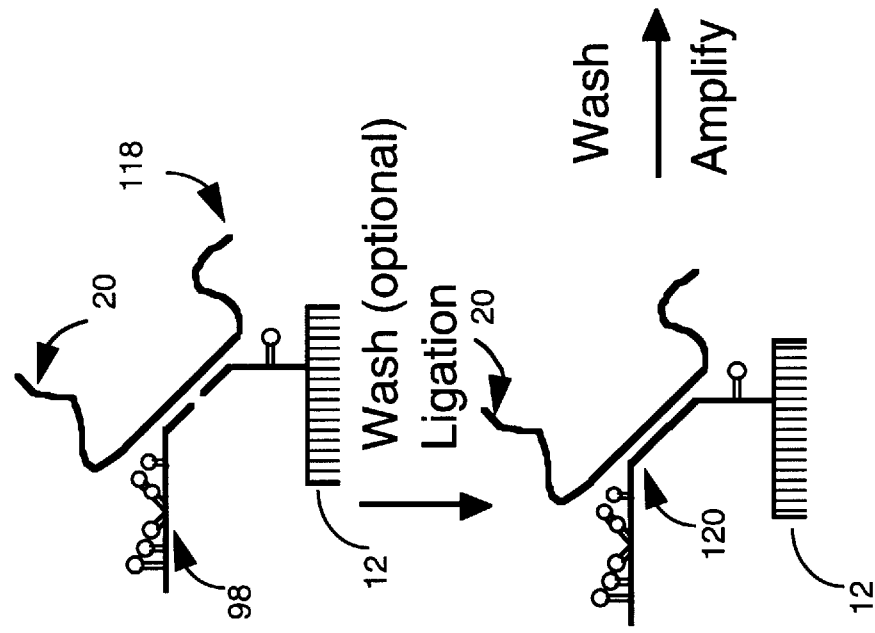

If desired, a washing step can be carried out to remove from the support 12 a substantial portion of unbound reactants and components of the sample. A ligation step can then be performed, in which the two half molecules 98 and 100 are covalently joined together to produce an amplifiable nucleic acid 120 (FIG. 4D). An important element of this step is that the ligation is dependent upon the correct hybridization of the two half probes 98 and 100 to the correct analyte nucleic acid 20. Methods involving the use of such half, or binary, probe systems are known in the art and are described, e.g., in European Patent Applications EP 94/906626.0 and EP 94/906682.3.

Following the ligation step, a high stringency wash can be carried out to remove remaining components of the sample and 3'-half molecules 98 that are not now covalently attached to the support 12. Remaining on the support are the originally bound 5'-half probes 100 and, at each location where a nucleic acid analyte has bound to a 5'-half probe 100, a replication competent, signal generating nucleic acid 120 (FIG. 4D), which, in this example, includes a replicable MDV sequence.

Amplification of the amplifiable nucleic acid 120 can be carried out as follows. Components of a QBR amplification reaction (i.e., QBR, nucleotide triphosphates, Mg++, appropriate salt, buffer, etc. (see, e.g., Moody et al., Biochemistry 33:13836–13847, 1994)) are well known, and are applied to the support along with, or as components of, a diffusion limiting matrix (e.g., agarose or another type of "gel" matrix, such as gelatin (e.g., KNOX), polyacrylamide gels, or mixtures thereof), which permits amplification of the ligated QBR detection probes 120 in the vicinity of each locus where a replication competent QBR molecule 120 has been formed. Importantly, each of the colonies of amplification product 124 form on the solid support in a locus corresponding to the presence of one nucleic acid analyte 20.

Amplification is allowed to proceed under appropriate conditions, such as temperature conditions, for a length of time appropriate to generate a discrete and discernable amount of an amplification product 122 (FIG. 4E). Such loci, or spots, 124 of amplified QBR probe RNA can be visualized by any of a number of methods known in the art, including, e.g., by detection of radioactivity, fluorescence, color, or a chemiluminescent substance incorporated into the amplification product 122. For example, a fluorescent intercalating dye, such as propidium iodide, can be added to the amplification mixture so that, as amplification product 122 is produced, the dye intercalates into the product 122, leading to production of an intense fluorescence at the site of amplification 124 (FIG. 4F).

The optimal length of time for the amplification reaction depends on a number of factors, which are well known to those skilled in the art, and include, e.g., the inherent replication rate of the QBR probe, the concentration of reactants in the amplification reaction (e.g., the QBR concentration, the DNTP concentration, and the Mg++ concentration), as well as the temperature at which the reaction is carried out (see, e.g., Burg et al., 1995, supra). The optimal reaction time also will depend upon the detection means used. Microscopic detection of fluorescence, for example, requires generation of only a very small spot. Macroscopic (e.g., visual) detection of amplified RNA may require less instrumentation, but bigger spots.

The number of spots of signal can be counted to quantitate the number of nucleic acid analyte molecules in the sample that was applied to the support. This can readily be determined, based on the volume of sample applied to the slide and the overall efficiency of the process. For example, each of the steps of the assay, e.g., hybridization of the analyte to the first (5'-half) probe on the solid support, hybridization of the second (3'-half) probe, and ligation, has a characteristic efficiency of less than 100%. Thus, for example, if 50% of the analyte nucleic acids applied to the device hybridize with both the 5' and 3'-half probes, and 50% of these are ligated, then 25% of the analyte molecules will lead to production of an amplifiable, ligated product. Thus, e.g., 1,000 analyte nucleic acid molecules applied to the device will produce about 250 spots of amplified signal.

Figure 5A:
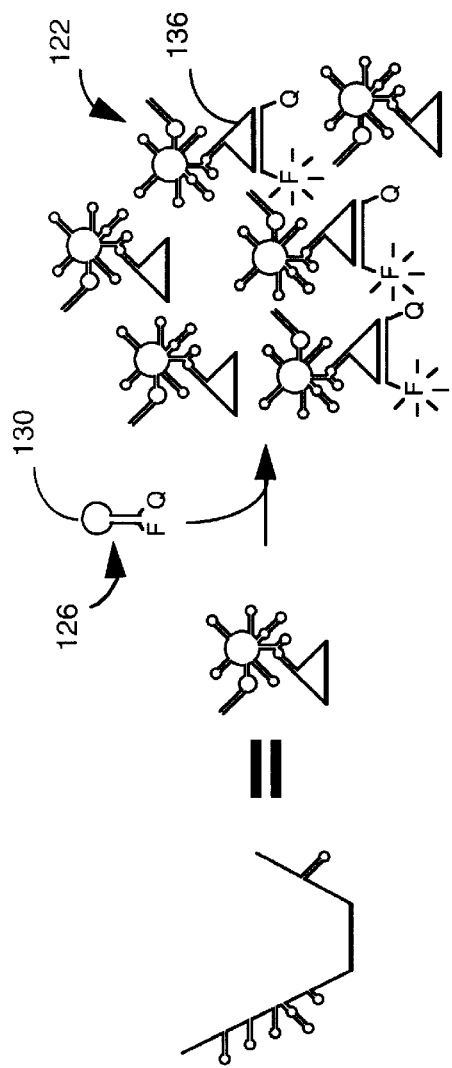
FIGS. 5A and 5B are schematic representations of two different methods of using a fluor-quencher pair, e.g., a fluorescence energy transfer pair, to detect an amplified nucleic acid product.

Two alternative detection means are illustrated in FIGS. 5A and SB and involve the use of a fluor-quencher pair, or, e.g., a fluorescence energy transfer pair, as described, for example, by Morrison (Detection of Energy Transfer and Fluorescence Quenching, in *Nonisotopic Probing, Blotting, and Sequencing,* Academic Press, 1995) and Tyagi et al. (Nature BioTechnology, 14:303–308, 1996). A fluorquencher pair consists of a fluorescent dye (labeled "F", e.g., fluorescein) and a quencher dye (labeled "Q"), which blocks emission of fluorescence from the fluorescent dye when the two dyes are in close proximity.

Figure 5B:
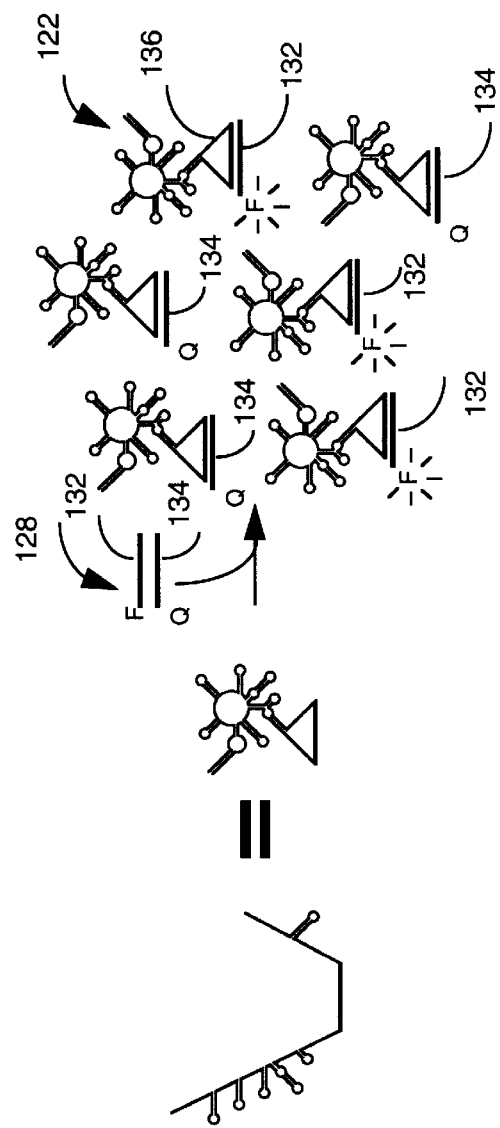

In application of this concept to nucleic acid detection, the fluorescent dye and the corresponding quencher dye are held in proximity to one another by attachment to a short nucleic acid (e.g., DNA) probe that self-associates (e.g., the "beacon" 126 in FIG. 5A, or the Morrison pair of probes 128 in FIG. 5B). The sequences in the loop structure 130 of the beacon 126, or of one of the oligonucleotides 132 and 134 in the Morrison pair 128, are designed so that they hybridize to a specific, predetermined target sequence in the amplified product 122. In this embodiment, these probe sequences hybridize to the probe portion 136 of the amplified product 122. When this occurs, the F and Q entities are forced apart by the rigid structure of the double-stranded hybrid, thus allowing fluorescence of the F entity to be detected (FIGS. 5A and SB).

Figure 6:
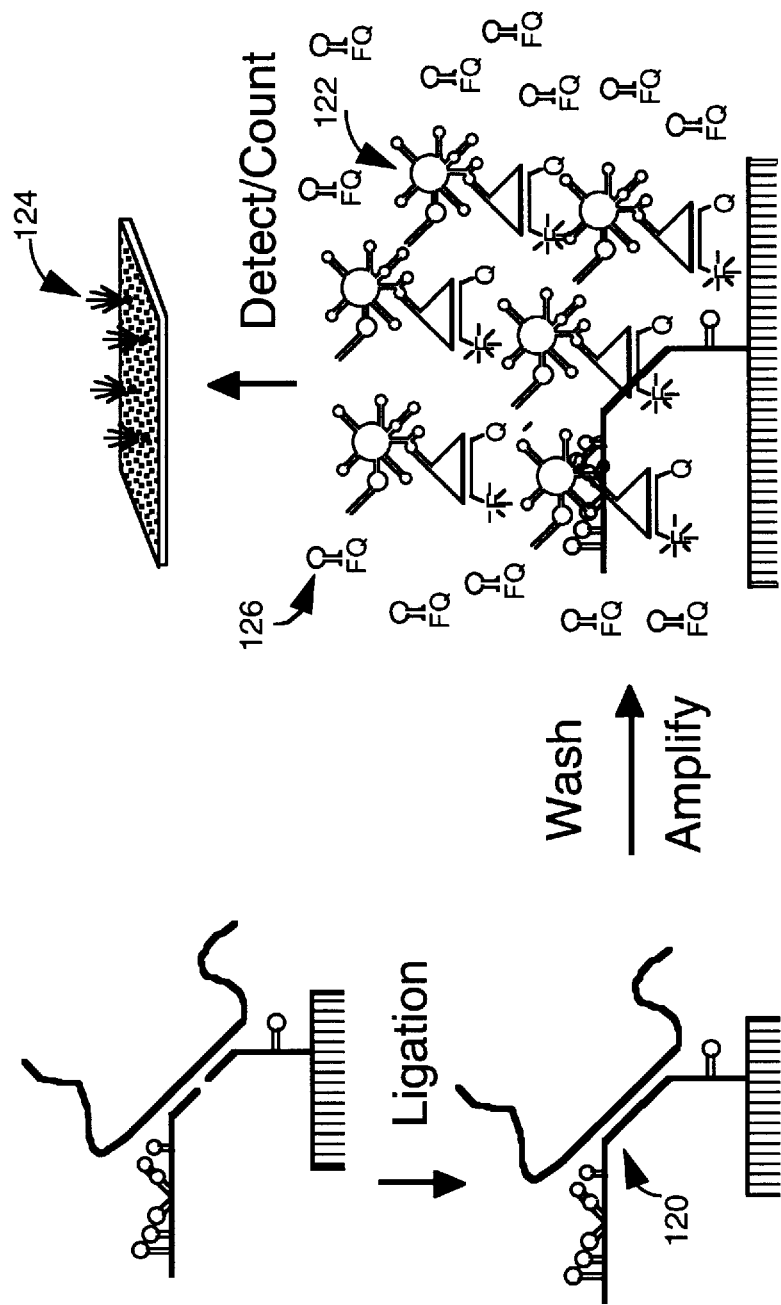
FIG. 6 is a schematic representation of a flow chart of the use of a fluor-quencher pair, e.g., a fluorescence energy transfer pair, to detect an amplified nucleic acid product formed by use of a device and method of the invention.

FIG. 6 illustrates the use of fluor-quencher pairs, or fluorescence energy transfer pairs, in the detection of specific QBR amplification products in the methods of the invention. In this example, beacon pair probes 126 (e.g., F =fluorescein, Q=4-(4'-dimethylaminophenylaza)benzoic acid (DABCYL)) are added to the amplification cocktail. As amplification of the initial ligated QBR probe product 120 proceeds, the beacon probes 126 hybridize to the amplification products 122, thus creating a detectable, fluorescent signal 124. An advantage of this type of detection strategy is that amplification of specific products can be detected. In other schemes, such as those employing an intercalator dye (e.g., propidium iodide), amplification can easily be detected, but the identity of the amplification product cannot.

An additional advantage of employing the beacon or Morrison probes for detection of amplification is that multiple colors of F:Q pairs can be designed and employed, so that amplification reactions can be examined for amplification of multiple types of pre-determined QBR probes. For example, in a further embodiment of the invention, means for the simultaneous quantitative detection of multiple analyte nucleic acids is provided. In this embodiment, the support contains a random distribution or field of multiple types of half probes having probe sequences that correspond to each of the nucleic acid analytes to be assayed. The same principles described above for diffusion of the analyte to the surface, ligation, and subsequent amplification apply, but in this embodiment, in each locus or spot where an analyte causes the formation of a replicable product, the amplification products arising from that spot will have a probe sequence corresponding to the target sequence that nucleated the ligation event. Accordingly, different analyte nucleic acid molecules will cause the amplification of different QBR probe molecules. Each specific probe molecule will have a sequence that is specific for the analyte required for its formation.

Multiple fluorescence energy transfer probes (beacons or Morrison probes), corresponding to multiple possible QBR probe sequences, and each carrying a distinguishable fluorescent moiety, are present during or added subsequent to the amplification reaction. These probes, upon hybridization to the amplified QBR RNA molecules in each spot, provide different colors, corresponding to each originating analyte molecule. Thus, multiple analyte nucleic acids can be detected and distinguished in a single homogeneous assay. This increases the power, flexibility, and cost effectiveness of such assays.

Variations in binary probe design that are within the scope of invention are illustrated in FIGS. 7A–7G. FIGS. 7A, 7B, and 7C illustrate alternative possible "alignments" of half probes 98 and 100 with a suspected point mutation (black arrowhead) in an analyte nucleic acid 20 that, in this example, contains a fusion between portions of BCR and ABL genes. FIG. 7D illustrates a ternary version of the QBR assay (using a third probe 138), which can be applied in this invention as well. The advantages of using ternary probe strategies include achieving higher specificity of hybridization than in binary probe strategies.

FIG. 7E shows the basic elements of an alternative assay format, in which a separate "capture" probe 140 (in this illustration attached to a bead or particle 142, such as a magnetic particle). This format is useful and convenient for enrichment of the analyte molecules 20 and removal of sample components, prior to ligation and amplification steps. Alternatively, magnetic particles can be used as the solid phase as shown in FIG. 7F and, following ligation and washing, dispensed into the diffusion limiting matrix for amplification. Other alternative assay formats are illustrated in FIGS. 7F and 7G, and are described above.

The methods described above employ the use of hybridization and washing conditions, such as "stringent" hybridization and washing conditions. Hybridization reactions are typically carried out under "stringent conditions," e.g., low to moderate stringency conditions, in which specific and some non-specific interactions can occur. After hybridization, washing can be carried under higher stringency conditions to eliminate non-specific binding. As is known in this field, optimal washing conditions can be determined empirically, e.g., by gradually increasing the stringency. Condition parameters that can be changed to affect stringency include, e.g., temperature and salt concentration. In general, the lower the salt concentration, pH, and chaotropic agent (e.g., guanidine thiocyanate) concentration, and the higher the temperature, the higher the stringency. For example, washing can be initiated at a low temperature (e.g., room temperature), using a solution containing an equivalent or lower salt concentration than the hybridization solution. Subsequent washing can be carried out using progressively warmer solutions having the same salt solution. Alternatively, the salt concentration can be lowered and the temperature maintained in the washing step, or the salt concentration can be lowered and the temperature increased. Such standard variations are known in the art. Additional parameters can be altered to affect stringency including, e.g., the use of a destabilizing agent, such as formamide.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a solid support, such as a glass plate or a filter.

An example of hybridization conditions that can be used in the methods of the invention involves hybridization at room temperature in 3×SSC, and subsequent washing in 3×SSC. Thus, in this example, the stringency is not varied from the hybridization to the wash. In another example, hybridization is carried out at room temperature in 3×SSC, and subsequent washes are carried out in 3×SSC at the following temperatures: 25° C., 42° C., 52° C., 58° C., and 70° C.

Another example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Attachment of probes, such as nucleic acid probes, to solid supports used in the invention can be carried out using any of a number of standard methods, including direct adsorption or chemical coupling to reactive groups on the surface. For example, a linker can be used, e.g., a flexible carbon chain, such as a 3-glycidoxypropyltrimethoxysilane linker (see, e.g., Maskos et al., Nucl. Acids Res. 20(7):1679–1684, 1992). Photolithography can also be used to attach the probes to the solid supports. In this method, the surface of the solid support is coated with a photosensitive linker and an appropriate light source, such as a laser beam, is directed at the region of the surface where the binding of the probe is desired. The probe is then contacted with the surface, where it binds to the light-activated region. This method readily permits the binding of different probes to a solid support.

As is discussed above, many different amplification schemes can be used in the invention (see, e.g., Pershing et al. (supra). For example, target amplification (e.g., PCR; Saiki et al., supra), a transcription-based amplification system (TAS; Kwoh et al., supra), the self-sustained sequence reaction (3SR; Guatelli et al., supra), transcription-mediated amplification (TMA; U.S. Pat No. 5,399,491; WO 93/22461), nucleic acid sequence-based amplification (NASBA; Compton, supra), strand displacement amplification (SDA; Walker et al., supra), or probe amplification (e.g., QBR (Lizardi et al., supra), ligase amplification reaction (LAR; Wu et al., supra), ligase chain reaction (LCR; Barany, supra)) can be used.

As is mentioned above, in embodiments in which autocatalytically replicable nucleic acids are used, many different types of such nucleic acids can be used in the invention. For example, midivariant RNAs (e.g., midivariant-1 (MDV-1)), minivariant RNA, microvariant RNA, and nanovariant RNA, can be used. The sequences of these and other autocatalytically replicable nucleic acids are well known in the art, and readily adaptable for use in the present invention (see, e.g., Mills et al., Proc. Natl. Acad. Sci USA, 72:4252–4256, 1975; Schaffner et al., J. Mol. Biol., 117:877–907, 1977; Kacian et al., Proc. Natl. Acad. Sci USA, 69:3038–3042, 1972; Chu et al., U.S. Pat. No. 4,957,858; Miele et al., J. Mol. Biol., 171:281–295, 1983). In addition, the secondary structures of autocatalytically replicable RNAs, such as MDV-1 and microvariant RNAs, both of which contain several stem structures, are well known in the art (see, e.g., Mills et al., supra; Nishihara et al., J. Biochem., 93:669–674, 1983). Based on this information, one skilled in the art can predict where compensatory base pair changes in the stem structures of these RNAs can be tolerated, thus identifying other molecules that can be used as autocatalytically replicable nucleic acids.

The autocatalytically replicable nucleic acids, which are templates for generating amplification products, can consist of RNA, DNA, or modifications or combinations thereof. The amplified products generated by QBR replication of such templates are RNA.

Detection of nucleic acid analytes using the devices and methods of the invention can be useful in fields such as medicine, forensics, agriculture, industry, food sciences, and veterinary medicine. For example, in the field of medicine, the methods of the invention can be used in the diagnosis of conditions (e.g., cancer) characterized by the presence or absence of specific nucleic acid markers and/or altered levels of normally occurring nucleic acids. The methods of the invention can also be used to detect gene mutations, which can be characterized by, e.g., single base pair changes, small or large deletions, insertions, or rearrangements (e.g., chromosomal translocations), and genetic polymorphisms. In addition, the methods of the invention can be used to detect the presence of an infectious pathogen (e.g., a bacterium, a virus, a protozoan, a parasite, or a fungus) or a rare cell (e.g., a fetal cell in maternal blood) in a sample, e.g., a sample from a patient. Finally, the devices, methods, and systems of the invention can be readily incorporated into a panel format for the detection and quantitation of multiple target analytes.

The following example describes the use of methods and devices of the invention in the diagnosis of a condition caused by a chromosomal translocation.

Chromosomal translocations and inversions commonly result in the juxtaposition of two genes (one from each of the chromosomes or chromosomal segments involved in the recombination) that normally are physically and transcriptionally separate from one another. Such translocations can result in the production of novel fusion proteins that can have adverse physiological effects. For example, a number of fusion proteins generated in this manner have been implicated in the etiology of cancer (see, e.g., Rabbits, Nature 372:143–149, 1994). The archetype for such a cancer-causing gene rearrangement is the chromosome 9-chromosome 22 translocation (t9;22) that results in formation of the so-called Philadelphia,, chromosome, the presence of which is strongly correlated with a number of leukemias, including chronic myelogenous leukemia (CML) and acute lymphocytic leukemia (ALL). At the molecular level, the translocation results in joining of the bcr gene on chromosome 22 to the abl gene on chromosome 9. Through normal transcription, splicing, and translation mechanisms, a hybrid BCR/ABL protein is produced from the hybrid gene, which causes elevated expression of the encoded tyrosine kinase enzymatic activity.

In CML, a minimum residual disease (MRD) state can persist for many years, in which only relatively low levels of the altered BCR/ABL protein are produced and during which no, or relatively minor, disease pathology is evident. Then, on average 4–5 years following the initial diagnosis, the disease escalates to an acute phase, which requires major medical intervention. The onset of this acute phase is presaged by an increase in expression of the fused BCR/ABL mRNA and protein. As understood in this field, medical intervention is most effective if it is initiated as soon as possible following the transition to the acute phase of the disease. Accordingly, a diagnostic test that can be used to quantitatively monitor the level of BCR/ABL MRNA expression in CML patients during the MRD state can be used in the management of their disease.

Because the level of BCR/ABL mRNA production can be quite low during the MRD state, and because it is desirable to detect the rise in expression level as early as possible, a highly sensitive assay is required for clinical utility. The present invention describes means of performing such monitoring using the QBR amplification system. For example, the present invention provides methods for monitoring the level of expression of gene fusions resulting from somatic rearrangement, e.g., leading to juxtaposition, of two genes that are normally physically and transcriptionally separate from one another. This clearly has application in the diagnosis of CML and ALL, as well as other diseases in which fusion proteins play a significant role, e.g., other hematopoietic cancers and solid tumors (Rabbits, 1994, supra).

FIG. 8 illustrates specific sequences of analyte-binding probe segments (SEQ ID NOs:1 and 2) that can be used in diagnostic methods for detecting mRNA transcribed from bcr/abl gene fusions (SEQ ID NO:3), according to the methods of the invention described above.

These probes can be used in, e.g., the following method. Cells in a peripheral blood sample from a patient are lysed in, e.g., guanidine thiocyanate. A 3'-half probe (50 ng/100 µL; e.g., a probe having the sequence of SEQ ID NO: 2; see FIG. 8) is added to the lysed sample, and the mixture is then applied to the surface of a solid support of the invention, to which is bound a probe having the sequence of, e.g., SEQ ID NO:1 (see FIG. 8), where hybridization is allowed to proceed for, e.g., about one hour. The surface of the solid support is then washed, e.g., by dipping the solid support (e.g., a glass plate) in buffer contained in a Copeland jar. Medium stringency conditions can be used for the wash, in which the support is incubated in fresh hybridization buffer, without probe, at 37° C. for 5 minutes. Ligation buffer and ligase is then added to the support, and incubation is carried out at about 37° C. for about five minutes. The support is then washed, e.g., in 0.05N NaOH for five minutes at 37° C., QBR and amplification reagents (dNTPs, Mg, Tris buffer pH 7.8), in a diffusion limiting matrix (e.g., polyacrylamide) are added, and amplification is carried out for about fifteen minutes. Spots generated in this reaction can be counted in a fluorescence microscope or by visual inspection, if the amplification is carried out for a sufficient length of time, so that the spots are, e.g., greater than about 1 mm in diameter.

The invention can be used in any circumstances in which detection of nucleic acids (DNA or RNA) encoding fusion-proteins is desired.

Other Embodiments

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. An assay device for detecting the presence of a nucleic acid analyte in a sample, said device comprising a planar, solid support having covalently bound thereto a two-dimensional field of analyte-specific nucleic acid probes, each probe comprising a first end covalently bound to said support and including a 5' portion of an autocatalytically replicable nucleic acid, and a second end including an analyte-binding segment.

2. The device of claim 1, wherein said autocatalytically replicable nucleic acid is replicable by Q-beta replicase.

3. The device of claim 2, wherein said autocatalytically replicable nucleic acid comprises a midivariant nucleic acid.

4. The device of claim 1, wherein said solid support is a glass plate.

5. A method for detecting the presence of a nucleic acid analyte in a sample, said method comprising the steps of:
    (a) applying the sample to a solid support having covalently bound thereto a two-dimensional field of first analyte-specific nucleic acid probes, each of the first probes comprising a first end bound to the solid support and including a 5' portion of an autocatalytically replicable nucleic acid, and a second end including a first analyte-binding segment, wherein the first analyte-binding segment of each of the first probes hybridizes to a first region of the analyte;
    (b) applying a second nucleic acid probe to the solid support, the second probe comprising a second analyte-binding segment that hybridizes to a second region of the analyte, the second probe further comprising a remainder of said autocatalytically replicable nucleic acid, wherein the first and second regions of the analyte are adjacent nucleotide segments, and wherein the analyte, the first probe, and the second probe hybridize together on the support to form a complex including a complete autocatalytically replicable nucleic acid;
    (c) applying a diffusion limiting matrix to the solid support;
    (d) amplifying the complete autocatalytically replicable nucleic acid to generate an amplified product; and
    (e) detecting the amplified product as a measure of the presence of the analyte in the sample.

6. The method of claim 5, further comprising the step of ligating the first and second probes in said complex together to form said complete autocatalytically replicable nucleic acid.

7. The method of claim 5, wherein the sample is applied to the solid support prior to being contacted with the second probe.

8. The method of claim 5, wherein the sample is contacted with the second probe prior to being applied to the solid support.

9. The method of claim 5, wherein the amplification step is carried out in the presence of a fluorescent intercalating dye and the detection step is carried out by monitoring the amplified product for the presence of the dye.

10. The method of claim 5, wherein the detection step is carried out by employing a fluor-quencher pair.

11. The method of claim 5, wherein multiple analytes are simultaneously detected in the sample and the detection step is carried out by employing multiple fluor-quencher pairs that comprise distinguishable fluorescent moieties.

12. The method of claim 5, wherein said autocatalytically replicable nucleic acid comprises a nucleic acid replicable by Q-beta replicase.

13. The method of claim 12, wherein said autocatalytically replicable nucleic acid comprises a midivariant nucleic acid.

14. The method of claim 5, further comprising washing said complex to remove any unbound first or second probes.

15. The method of claim 5, wherein said diffusion limiting matrix is selected from the group consisting of gelatin, agarose, polyacrylamide, and any combination thereof.

16. The method of claim 5, further comprising determining the concentration of the analyte in the sample.

17. The method of claim 5, wherein the amplification step generates a colony of amplified product, the colony being centered around the complete autocatalytically replicable nucleic acid; and wherein the concentration of the analyte in the sample is determined by counting colonies of amplified product formed on the solid support, and the number of colonies corresponds to the concentration of the analyte in the sample.

18. An assay system for detecting a nucleic acid analyte in a sample, said assay system comprising:
    (a) a planar solid support having covalently bound thereto a two-dimensional field of first analyte-specific nucleic acid probes, each of the first probes comprising a first end covalently bound to the solid support and including a 5' portion of an autocatalytically replicable nucleic acid, and a second end including a first analyte-binding segment, wherein the first analyte-binding segment of each of the first probes hybridizes to a first region of the analyte; and
    (b) a second nucleic acid probe comprising a second analyte-binding segment that hybridizes to a second region of the analyte, the second probe further comprising a remainder of the autocatalytically replicable nucleic acid, and the first and second regions of the analyte comprising adjacent nucleotide segments;
    wherein binding of the first and second probes to the analyte permits amplification of the autocatalytically replicable nucleic acid.

19. An assay system for detecting a nucleic acid analyte in a sample, said assay system comprising:
- (a) a solid support having bound thereto a two-dimensional field of capture probes, each of the capture probes comprising a capture segment that hybridizes to a capture region of the analyte;
- (b) a first nucleic acid probe comprising a first segment that hybridizes to a first region of the analyte;
- (c) a second nucleic acid probe comprising a second segment that hybridizes to a second region of the analyte; and
- (d) a diffusion limiting matrix for application to the solid support;

wherein binding of the capture probes and the first and second probes to the analyte permits amplification of a detectable product within the diffusion limiting matrix.

20. The assay system of claim 19, wherein the first and second regions of the analyte are adjacent nucleotide segments, said first nucleic acid probe further comprises a portion of an autocatalytically replicable nucleic acid molecule, and said second nucleic acid probe further comprises a remaining portion of said autocatalytically replicable nucleic acid molecule.

21. The assay system of claim 19, wherein the capture and first regions of the analyte are adjacent nucleotide segments and the capture and second regions of the analyte are adjacent nucleotide segments, said first nucleic acid probe further comprises a portion of an autocatalytically replicable nucleic acid molecule, and said second nucleic acid probe further comprises a remaining portion of said autocatalytically replicable nucleic acid molecule.

22. The method for detecting the presence of a nucleic acid analyte in a sample, said method comprising the steps of:
- (a) contacting the sample with the bound capture probes and the first and second probes of the assay system of claim 19, wherein the first and second regions of the analyte are adjacent nucleotide segments, the first probe further comprises a portion of an autocatalytically replicable nucleic acid molecule, the second probe further comprises a remaining portion of the autocatalytically replicable nucleic acid molecule, and the contacting permits the analyte, the first probe, and the second probe to hybridize together on the solid support to form a complex including a complete autocatalytically replicable nucleic acid;
- (b) applying a diffusion limiting matrix to the solid support;
- (c) amplifying the complete autocatalytically replicable nucleic acid to generate an amplified product; and
- (d) detecting the amplified product as a measure of the presence of the analyte in the sample.

23. A method for detecting the presence of a nucleic acid analyte in a sample, said method comprising the steps of:
- (a) contacting the sample with the bound capture probes and the first and second probes of the assay system of claim 19, wherein the capture and first regions of the analyte are adjacent nucleotide segments and the capture and second regions of the analyte are adjacent nucleotide segments, the first probe further comprises a portion of an autocatalytically replicable nucleic acid molecule, and the second probe further comprises a remaining portion of the autocatalytically replicable nucleic acid molecule, and the contacting permits the analyte, the first probe, and the second probe to hybridize together on the said support to form a complex including a complete autocatalytically replicable nucleic acid;
- (b) applying a diffusion limiting matrix to the solid support;
- (c) amplifying the complete autocatalytically replicable nucleic acid to generate an amplified product; and
- (d) detecting the amplified product as a measure of the presence of the analyte in the sample.

24. A method for detecting the presence of a nucleic acid analyte in a sample, the method comprising the steps of:
- (a) contacting the sample with a solid support having covalently bound thereto a two-dimensional field of first analyte-specific nucleic acid probes, each of the first probes comprising a first end bound to the support and including a second end including a first analyte-binding segment;
- (b) applying a diffusion limiting matrix to the support;
- (c) performing amplification by one of polymerase chain reaction, ligase chain reaction, transcription-mediated amplification, nucleic acid sequence-based amplification, and strand displacement amplification in a manner dependent upon the presence of both the first probe and the nucleic acid analyte, and in such a manner that the products of such amplification reaction are restrained to form localized foci within the diffusion limiting matrix on said support; and
- (d) detecting the amplified products as a measure of the presence of the analyte in the sample.

25. An assay system for detecting a nucleic acid analyte in a sample, said assay system comprising:
- (a) a solid support having covalently bound thereto a two-dimensional field of first analyte-specific nucleic acid probes, each of the first probes comprising a first end covalently bound to the solid support and including a 5' portion of an autocatalytically replicable nucleic acid, and a second end including a first analyte-binding segment, wherein the first analyte-binding segment of each of the first probes hybridizes to a first region of the analyte;
- (b) a second nucleic acid probe comprising a second analyte-binding segment that hybridizes to a second region of the analyte, the second probe further comprising a remainder of the autocatalytically replicable nucleic acid, and the first and second regions of the analyte comprising adjacent nucleotide segments; and
- (c) a diffusion limiting matrix for application to the solid support;

wherein binding of the first and second probes to the analyte permits amplification of the autocatalytically replicable nucleic acid within the diffusion limiting matrix.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

GGCTTTTGAA CTCTGCTTAA A                                  2 1

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

AGATGCTACT GGCCGCTGAA G                                  2 1

( 2 ) INFORMATION FOR SEQ ID NO:3:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:3:

UUUAAGCAGA GUUCAAAAGC CCUUCAGCGG CCAGUAGCAU CU        42